United States Patent [19]

Benneche et al.

[11] Patent Number: 4,596,870
[45] Date of Patent: Jun. 24, 1986

[54] SUBSTITUTED PYRIMIDIN-2-ONES AND THE SALTS THEREOF

[75] Inventors: Tore Benneche; Kjell Undheim, both of Oslo, Norway

[73] Assignee: Nyegaard & Co. A.S., Oslo, Norway

[21] Appl. No.: 337,988

[22] Filed: Jan. 8, 1982

[30] Foreign Application Priority Data

Jan. 9, 1981 [GB] United Kingdom ............... 810613

[51] Int. Cl.$^4$ ............... C07D 239/22; A61K 31/505
[52] U.S. Cl. ............................ 544/318; 544/316; 544/296
[58] Field of Search ............................ 544/316, 318

[56] References Cited

U.S. PATENT DOCUMENTS 4,399,140  8/1983  Gacek ........................... 424/251

Primary Examiner—Robert Gerstl
Attorney, Agent, or Firm—Bacon & Thomas

[57] ABSTRACT

Compounds of the general formula:

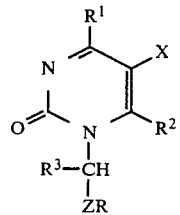

(wherein
X represents a halogen atom or a trifluoromethyl group;
$R^1$ and $R^2$ independently represent a hydrogen atom or a lower alkyl group;
Z is —O—, —S—, —SO—, —SO$_2$— or the group —NR$^4$— wherein R$^4$ is as defined for R hereinafter or represents the group COR$^5$ in which R$^5$ represents a hydrogen atom or an optionally substituted aryl, heterocyclic, aralkyl, lower alkyl or lower alkoxy group;
R represents a C$_{6-10}$ carbocyclic aromatic group or a heterocyclic group containing a 5–9 membered unsaturated or aromatic heterocyclic ring which ring contains one or more heteroatoms selected from O, N and S and optionally carries a fused ring which carbocyclic or heterocyclic group may carry one or more C$_{1-4}$ alkyl or phenyl groups, said groups being optionally substituted; or, where Z represents the group >NR$^4$, the group —ZR may represent a heterocyclic ring optionally carrying a fused ring and/or optionally substituted as defined for R; and
R$^3$ represents a hydrogen atom or a lower alkyl, lower alkenyl, lower alkynyl, lower alkanoyl, lower alkenoyl, C$_{7-16}$ aralkyl or C$_{6-10}$ arly group or a 5–9 membered unsaturated or aromatic heterocyclic ring); and, where acid or basic groups are present, the salts thereof; are useful in combating abnormal cell proliferation.

The compounds of the invention are prepared by inter alia alkylation, ring closure and oxidation.

8 Claims, No Drawings

SUBSTITUTED PYRIMIDIN-2-ONES AND THE SALTS THEREOF

The present invention relates to substituted pyrimidin-2-ones, the salts thereof, processes for their preparation and pharmaceutical compositions containing them.

Abnormal cell proliferation is present in a number of diseases such as cancers, leukaemias, cutaneous cellular proliferation, e.g. contact dermatitis or psoriasis, or auto-immune diseases where proliferation of lymphocytes leads to an undesirable immune response against some of the normal tissues of the body.

A number of drugs are known which combat abnormal cell proliferation by destroying the cells in one of the phases of cell-division in which they are particularly susceptible to such attack. In general, the cell-division cycle of both normal and abnormal cells includes a succession of phases, usually termed the G1, S, G2 and M phases, the last-mentioned being mitosis which in itself includes four well defined phases, prophase, metaphase, anaphase and telophase, related to the rearrangement of chromasomal material in the cell. In general, DNA synthesis takes place in the S phase, while protein synthesis takes place in the G1 and G2 phases. The S phase is usually significantly longer than the G1 and G2 mitotic phases.

However, the cells are not normally dividing synchronously and at the time of administration of a particular drug a random proportion of both normal and abnormal cells will be in a phase susceptible to attack. This means that the drug may be indiscriminate in its effects and if the treatment is at a dose level significantly effective against abnormal cells, a large number of body cells may also be irreversibly damaged.

The present invention is based, in part, on the concept of using a drug to arrest the cell-division cycle reversibly in a particular phase, namely the metaphase, so that during the period when an effective amount of the drug remains in the system, a large number of both normal and abnormal cells reach that phase and stop dividing. When the drug has been eliminated from the system, cell division is resumed by affected cells and is initially synchronous. However, the normal and abnormal cells usually divide at markedly different rates and, considering the cells affected by the drug, after a few hours the abnormal cells will be synchronously in one phase while the normal cells will be in another. It is then possible to administer a drug which is effective against cells in the phase reached by the abnormal cells but not effective against cells in the phase reached by the normal cells. Thus, for example, hydroxyurea and cytosine arabinoside are effective against cells in the S-phase, while vincristine and vinblastine are effective against cells in the mitotic phase.

We have found that the compounds of the invention as defined hereinafter are useful in combating abnormal cell proliferation; in particular the compounds have very good metaphase arresting ability which by virtue of its reversibility is of use for this purpose. A compound of formula I may possess a DNA synthesis inhibiting activity.

According to one aspect of the present invention, therefore, we provide compounds of general formula I,

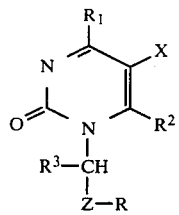

wherein

X represents a halogen atom, e.g. a fluorine, chlorine, bromine or iodine atom, or a trifluoromethyl group;

$R^1$ and $R^2$, independently represent a hydrogen atom or a lower alkyl group;

Z represents an oxygen atom or a sulfur atom or oxide thereof or a group $>NR^4$ (wherein $R^4$ is as defined for R hereinafter or represents the group $COR^5$ in which $R^5$ represents a hydrogen atom or an aryl, heterocyclic, aralkyl, lower alkyl or lower alkoxy group optionally substituted by one or more substituents selected from halogen atoms, hydroxyl, amino, oxo or $C_{1-4}$ alkyl groups.

R reprsents a $C_{6-10}$ carbocyclic aromatic group or a heterocyclic group containing a 5–9 membered unsaturated or aromatic heterocyclic ring which ring contains one or more heteroatoms selected from O, N and S and optionally carries a fused ring which carbocyclic or heterocyclic group may carry one or more $C_{1-4}$ alkyl or phenyl groups said group being optionally substituted by one or more substituents selected from halogen atoms, optionally substituted hydroxyl, optionally substituted amino, nitro oxo, sulfonic acid and sulfonamido groups and thioether groups and oxides thereof; or, where Z represents the group$>NR^4$, the group —ZR may represent a heterocyclic ring optionally carrying a fused ring and/or optionally substituted as defined for R;

$R^3$ represents a hydrogen atom or a lower alkyl, lower alkenyl, lower alkynyl, lower alkanoyl, lower alkenoyl, $C_{7-16}$ aralkyl or $C_{6-10}$ aryl group or a 5–9 membered unsaturated or aromatic heterocyclic ring; and where acid or basic groups are present, the salts thereof.

Certain compounds of formula I as hereinbefore defined and the salts thereof fall within the scope of the general disclosure of British Patent Specification No. 1,561,290, but there is no specific disclosure of any compound of the present invention. Moreover the compounds of the present invention possess especially good metaphase arresting ability compared with the compounds disclosed in British Patent Specification No. 1,561,290.

The term "lower alkyl", "lower alkoxy", "lower alkenyl" or "lower alkynyl" as used herein in relation to a group or part of a group (i.e. moiety) preferably relates to such groups or moieties containing up to 6, more preferably up to 4, carbon atoms.

The terms "aryl" and "carbocyclic aromatic" as used herein in relation to a group or part of a group (i.e. moiety) preferably relate to a phenyl or naphthyl group, especially a phenyl group. Thus the term "aralkyl" as used herein conveniently relates to an aralkyl group in which the alkyl moiety contains 1–6 carbon atoms and the aryl moiety is a phenyl or naphthyl group. Preferred aralkyl groups contain from 7 to 10 carbon atoms e.g. a benzyl group.

The term "heterocyclic ring" as used herein preferably relates to a ring having 5 to 7 ring members especially 5 or 6 ring members and is preferably an aromatic ring such as an imidazole, thiophene or pyrimidine ring. The heterocyclic ring may have another ring fused to it which ring may be carbocyclic e.g. phenyl.

The term "optionally substituted hydroxyl" as used herein includes alkoxy and aralkoxy, the alkyl and aralkyl moieties of which may be as defined above and where hydroxy groups are present on adjacent carbon atoms a single substituent may link both oxygen atoms, as in the alkylidene e.g. methylidene group, to form an alkylidenedioxy e.g. methylenedioxy group. The term "optionally substituted hydroxyl" preferably relates to a $C_{1-4}$ alkoxy group. The term "optionally substituted amino" as used herein includes amino groups carrying either one or two alkyl, aralkyl, aryl, lower alkanoyl, aralkanoyl, or aroyl groups, as well as cyclic imido groups derived from dibasic alkanoic, aralkanoic and aroic acids.

The term "halogen" is used herein to mean fluorine, chlorine, bromine or iodine.

The term "lower alkanoyl" is used herein to include not only alkanoyl groups in which the carbonyl group carries a lower alkyl group having 1 to 6 carbon atoms but also formyl groups. The terms "aralkanoyl" and "aroyl" refer to aryl groups in which the carbonyl group carries an aralkyl or aryl group as defined above.

It will be appreciated that when an oxo group is situated on a carbon atom carrying an optionally substituted hydroxyl or optionally substituted amino group, these will together constitute a carbonyl function such as a carboxy, esterified carboxy or carboxamido group.

It will be appreciated that the substituents listed in the definition of R may be present on the carbocyclic aromatic group, on the unsaturated or aromatic heterocyclic group, on any fused rings or on any $C_{1-4}$ alkyl or phenyl substituents present on said carbocyclic aromatic or unsaturated or aromatic heterocyclic groups. Thus for example the group R may represent a carbocyclic or heterocyclic group substituted by a haloalkyl group such as a perfluoroalkyl e.g. a trifluoromethyl group or by a hydroxyalkyl e.g. hydroxymethyl group.

$R^1$ and/or $R^2$ may represent a lower alkyl e.g. methyl group, but preferably $R^1$ and $R^2$ each represent a hydrogen atom.

$R^3$ preferably represents a lower alkyl, e.g. methyl group, a lower alkanoyl e.g. acetyl group, or a $C_{6-10}$ aryl group e.g. a phenyl group, but is especially hydrogen.

X preferably represents a halogen atom e.g. a chlorine atom.

Z may for example represent a sulphoxide or sulphone grouping or the group $NR^4$ in which $R^4$ represents a lower alkoxycarbonyl group e.g. an ethoxycarbonyl group or a lower alkanoyl group, e.g. a formyl or acetyl group, but Z advantageously represents an oxygen or sulphur atom.

R preferably represents a naphthyl or, more preferably a phenyl group optionally substituted by one or more substituents selected from halogen, lower alkyl, lower alkoxy, lower haloalkyl, lower hydroxyalkyl, lower alkoxycarbonyl, nitro and lower alkanoyl. Thus for example R may represent an unsubstituted phenyl group or a phenyl group substituted by fluorine, chlorine, methyl, methoxy, trifluoromethyl, hydroxymethyl, methoxycarbonyl, nitro and/or acetyl. Substituents on the phenyl ring may be present, for example, in the 2-, 3- and/or 4- positions as in the 4-chlorophenyl, 2,4-dichlorophenyl, 4-fluorophenyl and 3-tolyl groups.

R may also advantageously represent a 5- or 6- membered heterocyclic ring containing, for example, one or more nitrogen or sulphur atoms and optionally carrying a fused ring such as a benzene ring. Examples of such rings include pyrimidinyl or imidazolyl rings e.g. pyrimidin-2-yl or imidazol-2-yl groups optionally substituted by lower alkyl groups e.g. methyl groups and/or by halogen atoms such as chlorine atoms as, for example in chloropyrimidin-2-yl groups and methylimidazol-2-yl groups; particular groups of this type include the 5-chloropyrimidin-2-yl and 1-methyl imidazol-2-yl groups. Further examples of such rings include optionally substituted thiophenyl groups which may carry a fused ring as in the benzothiophenyl group.

Where Z represents the group $NR^4$ the group —ZR may represent a heterocyclic ring optionally carrying a fused ring and/or optionally substituted as defined for R such as a pyrimidine ring optionally substituted by an oxo group and/or a halogen atom e.g. chlorine such as a 5-chloro-pyrimidin-2-on-1-yl group.

Preferred compounds of the present invention based on their activity include compounds of formula I in which R represents a phenyl group substituted by halogen, e.g. fluorine but especially chlorine, lower alkyl e.g. methyl, lower alkoxy e.g. methoxy or nitro; $R^1$, $R^2$ and $R^3$ each representing hydrogen and Z representing an oxygen or sulphur atom.

Especially preferred compounds of the present invention by virtue of their especially favourable metaphase arresting ability are (1) 1-(4-chlorophenoxy)methyl-5-bromopyrimidin-2-one;

(2) 1-(3-tolylsulphenyl)methyl-5-chloropyrimidin-2-one;

(3) 1-(4-methoxyphenylsulphenyl)methyl-5-chloropyrimidin-2-one;

(4) 1-(4-nitrophenylsulphenyl)methyl-5-chloropyrimidin-2-one; and (5) 1-(4-chlorophenoxy)methyl-5-iodopyrimidin-2-one.

The latter named compound (compound no. 5) is particularly preferred.

Where the compounds of formula I contain an acidic group, salts may be formed for example with alkali metal or alkaline earth metals, such salts including for example sodium, potassium, magnesium or calcium or ammonium (including substituted ammonium) salts. Compounds according to the invention carrying hydroxy or amino groups may also in general, possess enhanced water-solubility, the latter, or course, forming acid addition salts for example with mineral acids such as e.g. hydrochloric or sulphuric acid or organic acids such as e.g. acetic, tartaric or citric acid.

It will be appreciated that the compounds according to the invention, depending on the groups present, may exist in optical forms and all such forms as well as mixtures thereof are included within the scope of the invention.

It will be further appreciated that, for pharmaceutical use, the salts referred to above will be physiologically compatible but other salts may find use, for example in the preparation of compounds of general formula I and, where acidic or basic groups are present, their physiologically compatible salts.

The compounds of the invention are structurally quite simple and may be prepared by a variety of different processes. Reactions for the preparation of the sixmembered pyrimidine ring system from ureas and three carbon atom components are well known in the art.

According to another aspect of the invention, therefore, we provide the following process for the preparation of compounds of formula I as defined above:

Reaction (a)

A compound of formula II,

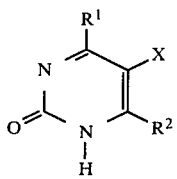
II (wherein X, R1 and R2 are as hereinbefore defined) or a salt thereof is reacted with an agent or agents serving to introduce the group

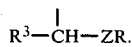

This agent may be of the formula

 III

[wherein R, Z and R³ are as hereinbefore defined and Y represents a leaving atom or group e.g. a halogen atom, a hydroxy or mercapto group, a reactive ether or ester derivative or an amino or substituted amino group (as hereinbefore defined)]

A compound of formula III is advantageously used in which Y represents an iodine, bromine or chlorine atom or a hydrocarbonsulphonyl derivative such as a mesylate, brosylate or tosylate.

A compound of formula III may also, for example, be used in which Y represents a group —ZR, the group being chosen such that the compound of formula III is a symmetrical acetal or its sulfur or nitrogen analogue.

The reaction between the compounds of formula II and III is conveniently effected in the presence of a polar solvent such as an alkanol e.g. ethanol or dimethylformamide. The reaction may also conveniently be effected in the presence of a base, e.g. a tertiary organic base such as triethylamine conveniently in the presence of a halogenated hydrocarbon such as dichloromethane or an ether; or in the presence of an inorganic base e.g. an alkali metal hydroxide, such as potassium hydroxide, or an alkali metal carbonate, such as sodium carbonate, in the presence of a phase transfer catalyst such as benzyltrimethyl-ammonium chloride. Where a salt of the compound of formula (II) is used, an added base will not normally be required. Such a salt may, for example, be an alkali metal, e.g. sodium or potassium salt.

The group of formula —CHR³ZR may also be introduced by a two stage reaction in which the compound of formula (II) is reacted with an O-silylating agent such as a bis(trialkylsilylamine) e.g. a bis(trimethylsilylamine) to form an O-silyl derivative, e.g. a trialkylsilyl ether such as a trimethylsilyl ether; followed by reaction with a compound of formula (III), preferably at an elevated temperature and conveniently in the absence of base. The reaction may also be effected, in the presence of a Lewis acid.

Where the reaction is effected at an elevated temperature the temperature is advantageously within the range 80° to 160° C. e.g. about 120° C. This two stage reaction involving O-silylation is especially advantageous since this process leads to selective N-alkylation thus substantially avoiding the formation of unwanted O-alkylated products which would otherwise significantly reduce the yield of the compound of formula I.

The reagent serving to introduce the group R³—CH—ZR may, as indicated above, also be an alcohol of the formula R³—CHOHZR or a derivative thereof. It will be appreciated that the effective alkylating agent may be formed by loss of the hydroxyl group. In this case the reaction is carried out in the presence of a condensing agent such as an acetal of a $C_{1-5}$ dialkylformamide e.g. dimethyl formamide. The alkyl groups of the acetal are preferably neopentyl groups, thus dimethylformamide dineopentylacetal is a preferred condensing agent.

Alternatively, the compound of formula III may be in the form of an acetal of a $C_{1-5}$ dialkylformamide carrying at least one acetal group derived from the alcohol R³—CHOHZR.

The compounds of formula (II) used as starting materials in reaction (a) may, for example, be prepared as described in our British Pat. No. 1,561,290. It is, however, difficult to prepare a 5-trifluoromethylpyrimidin-2-one of formula II by introduction of a trifluoromethyl group into the pyrimidin-2-one ring while direct ring closure methods are generally rather inefficient. We have now discovered that a 5-trifluoromethylpyrimidin-2-one of formula II may be prepared in good yield by hydrolysis of a compound of the formula:

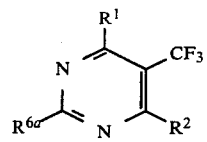 IV (wherein R¹ and R² are as herein defined and R⁶ᵃ represents a halogen atom or a group —SR⁶, —SOR⁶ or —SO₂R⁶ in which R⁶ represents a hydrocarbyl group such as a $C_{1-32}$ saturated or unsaturated, straight or branched, cyclic or acyclic aliphatic group or an araliphatic or heterocyclic substituted aliphatic group, a heterocyclic group or an aryl group which groups may if desired carry one or more substituents selected from halogen atoms and oxo, nitro, hydroxy, etherified hydroxy, esterified hydroxy, primary, secondary or tertiary amino, acylamino, etherified mercapto or —SO or —SO₂ derivatives thereof and esterified phosphonic acid groups) and where an acidic or basic group is present, the salts thereof.

The process is preferably effected by the use of a sulfone of formula IV in which R⁶ᵃ represents the group —SO₂R⁶ wherein R⁶ is as hereinbefore defined.

The sulphones of formula IV may be obtained, as described hereinafter, from a known compound 2-chloro-5-trifluoromethylpyrimidine.

Analogues of the sulfones of formula IV having a halogen atom in the 5-position of the pyrimidine ring have been described in detail in our European Patent Application No. 81300098.1 (Publication No. 33195) and preferred definitions of the group R in formula IV above are given in detail in relation to the group R in formula I in our above-mentioned European Patent Application. A compound of formula IV herein is preferably used however in which $R^6$ represents an alkyl e.g. lower alkyl group (for example with 1 to 6 carbon atoms) such as an ethyl or methyl group.

The hydrolysis of the compounds of formula IV as hereinbefore defined is conveniently effected by the use of a base such as an alkali metal hydroxide e.g. sodium or potassium hydroxide. The hydrolysis is conveniently effected at a temperature within the range 0° to 30° C. e.g. at ambient temperature.

The sulphone of formula IV is conveniently prepared by a method analogous to that described in our European Patent Application No. 81300098.1 (Publication No. 33195). Thus for example the compound of formula IV may be prepared by oxidation of the corresponding sulphide of the formula:

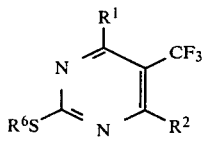
V (wherein $R^1$, $R^2$ and $R^6$ are as hereinbefore defined) by any convenient method including the use of (1) a manganese oxidising agent, for example a permanganate preferably potassium permanganate, convenienty in the presence of an acid e.g. acetic acid; (2) the use of chlorine or a hypochlorite e.g. sodium hypochlorite in an aqueous solution of the sulfide or sulfoxide; or (3) the use of a peroxide or peracid oxidising system such as hydrogen peroxide conveniently in the presence of an acid e.g. acetic acid advantageously at ambient temperature, or more preferably, m-chloroperbenzoic acid conveniently in the presence of a solvent e.g. dichloromethane and advantageously at a temperature from $-30°$ C. to $+30°$ C. conveniently at ambient temperature, or the use of a molybdenum peroxide conveniently in the presence of water and/or hexamethyl-phosphoramide.

The compound of formula V is conveniently prepared by reaction of a compound of formula:

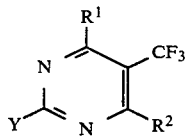
VI (wherein $R^1$, $R^2$ and X are as hereinbefore defined and Y represents a leaving atom or group) with a thiol of the formula $R^6SH$ or a thiolate of the formula

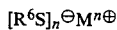
VII (wherein $R^6$ is as hereinbefore defined, M represents the stabilising cation and n represents the charge on the cation) whereby a compound of formula I in which n is 0 is obtained.

The reaction of the compound of formula VI with the compound of formula VII is conveniently effected by the use of a compound of formula VI in which Y represents a halogen atom e.g. a chlorine or bromine atom. The reaction is a nucleophilic substitution reaction, the nucleophile being in the form $R^6S^-$ and thus where the compound of formula VII is used in the form of a thiol, the reaction is preferably effected in the presence of a base sufficiently strong to remove the thiol proton to give the aforementioned nucleophile. Preferred bases include alkoxides, for example alkali metal and alkaline earth metal alkoxides such as sodium or potassium alkoxides e.g. ethoxides. The reaction is conveniently effected at an elevated temperature preferably at the reflux temperature of the reaction mixture.

The compound of formula VI has been described by A. Serban et al (German OLS No. 2,820032).

The compounds of formula II in which X represents a trifluoromethyl group are important intermediates for example in the preparation of the compounds of formula I in which X represents a trifluoromethyl group and have not been specifically described in the literature. These compounds thus constitute a further feature of the present invention.

Moreover the compounds of the formula:

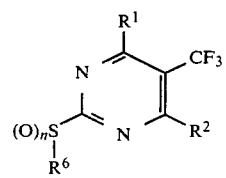
IVa (wherein $R^1$, $R^2$ and $R^6$ are as hereinbefore defined and n is 0, 1 or 2) and, where an acidic or basic group is present, the salts thereof are 5-trifluoromethyl analogues of the 5-halo derivatives described in our above European Patent Application possessing the ability to inhibit cell proliferation particularly by the inhibition of DNA synthesis. These compounds may thus be of interest for use against proliferating cells in the S-phase and may be employed as described in our above European Patent.

The compounds of formula III may be prepared by conventional techniques, but in the following cases we have found it particularly advantageous to prepare the compounds by the following methods:

(i) for the preparation of compounds of the formula

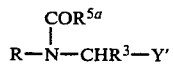
VIII (wherein R and $R^3$ are as hereinbefore defined, $R^{5a}$ represents a lower alkoxy group and Y' represents a chlorine or bromine atom), the reaction of a compound of the formula:

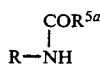
IX (wherein R and $R^{5a}$ are as hereinbefore defined) with a compound of the formula:

  $R^3CHO$
X (wherein $R^3$ is as herein defined) in the presence of a chlorinating or brominating agent such as for example thionyl chloride or thionyl bromide.

The reaction may for example be effected as described in German Offenlegungsschrift No. 2,119,518 and is conveniently effected in the presence of an ether or hydrocarbon, for example benzene, advantageously at ambient temperature.

The compound of formula IX may for example be prepared by reaction of a compound of the formula RNH$_2$ with a compound of the formula Hal COR$^{5a}$ wherein R and R$^{5a}$ are as hereinbefore defined and Hal represents a halogen atom e.g. a chlorine atom. The compound of formula IX may also be prepared by reaction of a compound of the formula RNCO with a compound of the formula R$^{5a}$H.

(ii) For the preparation of compounds of formula III in which Z represents a sulphur atom and Y represents a halogen atom, the reaction of a compound of the formula RSH (wherein R is as hereinbefore defined) with a compound of the formula:

   Hal—CHR$^3$—Hal'   XI (wherein R$^3$ is as hereinbefore defined and Hal and Hal' each represents a halogen atom).

A compound of formula XI is preferably used in which Hal and Hal' are different. Thus, for example, Hal may represent a chlorine atom whilst Hal' represents a bromine atom as in bromochloromethane.

The reaction may for example be effected as described in U.S. Pat. No. 2,827,492. The reaction is conveniently effected in the presence of an acid binding agent such as a trialkylamine e.g. triethylamine, advantageously at ambient temperature.

Where it is desired to use a compound of formula III in which Z represents SO or SO$_2$, such compounds may be prepared by oxidation of the corresponding sulphenyl compound of formula III by the methods described in our European Patent Application No. 81300098.1 referred to hereinbefore. It may however be preferable to prepare a compound of formula I in which Z represents a sulphur atom and to subsequently oxidise such compound to a compound of formula I in which Z is SO or SO$_2$ according for example to method (d) described hereinafter.

Compounds of formula III are, in fact, generally described and characterised in J. Hayami, N. Tanaka, S. Kurabayashi, Y. Kotani and A. Kaji; Bull. Chem. Soc. (Japan) 44, 3091 (1971).

(iii) For the preparation of compounds of formula III in which Z represents an oxygen atom and Y represents a halogen atom, the decarbonylation of a compound of the formula:

RO—CHR$^3$COHal   XII wherein R and R$^3$ are as hereinbefore defined and Hal represents a halogen atom.

The decarbonylation is conveniently effected in the presence of a rhodium (Rh$^I$) catalyst, advantageously a Rh$^I$P$^{III}$ catalyst such as a triarylphosphine rhodium halide e.g. a triphenylphosphine rhodium halide such as the chloride. The decarbonylation is conveniently effected at an elevated temperature, for example, at a temperature of from 120° to 200° C. e.g. 140° to 180° C.

The compound of formula XII may for example be prepared by reaction of the corresponding carboxylic acid with an appropriate halogenating agent such as thionyl chloride or thionyl bromide.

(iv) For the preparation of compounds of formula III in which R$^3$ represents a lower alkanoyl or lower alkenoyl group and in which Y represents a halogen atom, the halogenation of a corresponding compound of the formula:

   RZ—CH$_2$—R$^3$   XIII (wherein R and Z are as hereinbefore defined).

The halogenation is conveniently effected by the use of a halogenating agent such as N-bromo-succinimide conveniently in the presence of a free radical initiator such as 2,2'-azobis(2-methylpropionitrile).

A compound of formula XIII may for example be used in which Z represents an oxygen atom.

(v) For the preparation of compounds of formula III in which Y represents a halogen atom, the halogenative cleavage of a compound of the formula:

RZ—CHR$^3$—S—R$^7$   XIV wherein R, Z and R$^3$ are as hereinbefore defined, and R$^7$ represents an aryl group.

A compound of formula XIV is preferably used in which R$^7$ represents a 4-chlorophenyl group.

Halogenative cleavage is preferably effected by the use of a halogenating agent such as sulfuryl chloride or sulfuryl bromide conveniently in the presence of a solvent such as a halogenated hydrocarbon e.g. dichloromethane, advantageously at ambient temperature. The cleaved moiety —SR$^7$ is conveniently trapped as an adduct for example using cyclohexene or styrene.

The compound of formula XIV is preferably first prepared by reaction of a compound of the formula RZH with a compound of the formula R$^7$—S—Y wherein R, Z and R$^7$ are as hereinbefore defined and Y represents an atom or group removable as anion e.g. a halogen atom such as a chlorine or bromine atom. The reaction is preferably effected in the presence of a base such as an alkoxide for example a t-butoxide e.g. potassium t-butoxide. The reaction is also preferably effected in the presence of a dialkylformamide such as dimethylformamide.

Reaction (b)

Reaction of a compound of the formula:

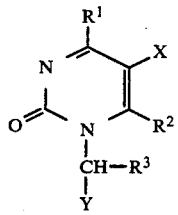   XV (wherein R$^1$, R$^2$, R$^3$, X and Y are as hereinbefore defined) with an agent or agents serving to introduce the group —Z—R. This agent may, for example, be a compound of the formula R—ZH.

A compound of formula XV is preferably used in which Y represents a halogen atom, a hydroxyl group, a mercapto group, an activated ether or ester or an amino function. If desired Y may represent a group —ZR (Z and R being as hereinbefore defined) in which case the reaction becomes an exchange reaction, the reaction conditions being chosen to promote the exchange.

The reaction is conveniently effected in the presence of an acid or a base.

The compounds of formula XV used as intermediates in this process may be prepared by methods analogous to those described in (a) above and (c) below.

The compound of formula XV may also for example be prepared by the halogenative cleavage of a compound of formula I in which Z represents a sulphur atom and R represents a hydrocarbyl group e.g. an aryl group. A compound of formula I is preferably used in which $R^7$ represents a 4-chlorophenyl group. The halogenative cleavage is preferably effected as described in process (v) for the preparation of compounds of formula III.

Reaction (c)

A compound of the formula:

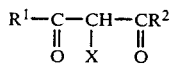    XVI (wherein X, $R^1$ and $R^2$ are as hereinbefore defined) or a functional derivative thereof such as an enol, acetal, enol ether, enol thioether, imine or enamine derivative, is reacted with a reagent serving to replace the oxo groups or functionally equivalent groups in formula V by a urea moiety

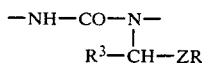

(wherein R, $R^3$ and Z are as hereinbefore defined).

It will be appreciated that any reactive groups, e.g. oxo groups, present in R, $R^3$ and/or Z which it is desired should not react may be protected by methods which are known from the literature, the protecting group(s) being removed following the cyclization reaction.

In one variation, the compound of formula XVI is reacted with a urea derivative of the formula:

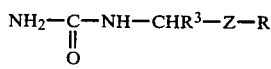    XVII (wherein Z, R and $R^3$ are as hereinbefore defined).

The reaction of the compounds of formula XVI and XVII may conveniently be effected in a solvent such as, for example, an alcohol, e.g. ethanol. The reaction proceeds at room temperature in the case where $R^1$ represents a hydrogen atom i.e. using a trifluoromethyl- or halo-malondialdehyde.

The urea reagent of formula XVII may, if desired, be replaced by a cyanamide of formula:

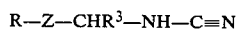

(wherein R and $R^3$ are as hereinbefore defined) which reacts to form an intermediate of formula:

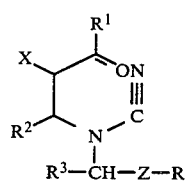    XVIII (wherein Z, R, $R^1$, $R^2$, $R^3$ and X are as hereinbefore defined) which may readily be cyclised, for example, in the presence of water.

Reaction (d)

Oxidation of a compound of formula I as hereinbefore defined wherein Z represents a sulfur atom to form a compound of formula I in which Z represents an SO or $SO_2$ group.

The oxidation of the compound of formula I may be effected by any convenient method including the use of a peroxide or peracid oxidising system such as (1) hydrogen peroxide advantageously at ambient temperature; (2) m-chloroperbenzoic acid conveniently at a low temperature; (3) molybdenum peroxide conveniently in the presence of water and/or hexamethyl-phosphoramide but especially (4) hydrogen peroxide and selenium dioxide, for example under neutral conditions.

In general each oxidation method may be employed to prepare either the sulfone or the sulfoxide, the reaction conditions e.g. reaction time, temperature or excess of reagent being altered depending upon the desired product. Thus if it is desired to prepare the sulfone, longer reaction times, higher temperatures and/or excess of the oxidising agent may for example be used.

The above-mentioned oxidation to form sulfoxides and/or sulfones may, if desired, be effected using intermediates, which contain Z in the form of a sulfur atom, and which are of use in preparing the compounds of formula I as hereinbefore defined.

According to a further feature of the present invention there are provided pharmaceutical compositions comprising as active ingredient, at least one compound of formula I as hereinbefore defined or, where an acidic or basic group is present a physiologically compatible salt thereof in association with a pharmaceutical carrier or excipient.

For pharmaceutical administration the compounds of general formula I and, where acidic or basic groups are present, their physiologically compatible salts may be incorporated into the conventional preparations in either solid or liquid form.

The compositions may, for example, be presented in a form suitable for rectal, parenteral or topical administration. Preferred forms include, for example suspensions, suppositories, creams, ointments and lotions and solutions e.g. for injection or infusion or for ingestion by the gastro-intestinal tract. Solutions for injection are especially preferred.

The active ingredient may be incorporated in excipients customarily employed in pharmaceutical compositions such as, for example, talc, gum arabic, lactose, starch, magnesium stearate, cocoa butter, aqueous or non-aqueous vehicles, fatty substances of animal or vegetable origin, paraffin derivatives, glycols, various wetting, dispersing or emulsifying agents and/or preservatives.

Advantageously the compositions may be formulated as dosage units, each unit being adapted to supply a fixed dose of active ingredient. Suitable dosage units for adults contain from 50 mg to 1.0 g of active ingredient. The dosage, which may be varied according to the compound used, the subject treated and the complaint concerned, may, for example, be from 0.25 to 7.0 g in a day in adults.

It will normally be necessary to have a knowledge of cell cycle kinetics (for example as determined by cytofluorography) of both the normal and abnormal cells and to prepare time schedules which indicate how long after administration of the drug the majority of the abnormal cells will reach a phase which is susceptible to attack by a chosen cytotoxic drug while the majority of normal cells are in a non-susceptible phase. These periods will naturally differ widely. Suitable cytotoxic drugs include cytosine arabinoside and hydroxyurea which are cytotoxic against cells in the S-phase. Since the S-phase is generally longer than the other phases, it is easier to find appropriate time schedules when using cytotoxic drugs in this phase.

The following Examples are given by way of illustration only:

Preparation 1

1-Chloromethylthio-4-methoxybenzene

4-Methoxythiophenol (40 mmol) was dissolved in bromochloromethane (0.8 mol) and triethylamine (40 mmol) added dropwise with stirring and external cooling to keep the reaction below room temperature. Once the addition was completed the reaction mixture was stirred at room temperature for 1 h. The mixture was then washed with water, the organic solution dried (MgSO$_4$), the solvent evaporated off and the residue distilled; yield: 3.90 g (52%), b.p. 70° C./0.01 mmHg. The physical data for the title compound are detailed in J. Hayami, N. Tanaka, S. Kurabayashi, Y. Kotani and A. Kaji; Bull. Chem. Soc. (Japan) 44, 3091 (1971).

Preparation 2

Chloromethoxybenzene

Tris(triphenylphosphine) rhodium chloride (0.1 mmol) was added to freshly distilled phenoxyacetyl chloride (28 mmol) and heated at 170° C. for 30 min before the mixture was distilled under vacuum to give chloromethoxybenzene (3.10 g). Yield: 78%. b.p. 71°-72° C./10 mm Hg (lit.b.p.: 86°-87° C./17 mm Hg see J. Hayami, N. Tanaka, S. Kurabayashi, Y. Kotani and A. Kaji; Bull. Soc. Chem. Japan 44, 3091 (1971).

Preparation 3

1-Chloromethoxy-4-chlorobenzene

Method A

Tris(triphenylphosphine)rhodium chloride (0.1 mmol) was added to freshly distilled 4-chlorophenoxyacetyl chloride (28 mmol) and heated at 170° C. for 30 minutes. The mixture was then distilled under vacuum to give 4-chloro-1-chloromethoxybenzene (4.10 g). Yield: 83%, b.p. 39°-41° C./0.01 mm Hg (lit. b.p.: 87°-88° C./6 mm Hg see H. J. Barber, R. F. Fuller, M. B. Green and and H. T. Zwartouw; J. Appl. Chem 3, 266 (1953).

Method B

Synthesis of the intermediate 1-(4-chlorophenylthio)methoxy-4-chloro-benzene

1-Bromomethylthio-4-chlorobenzene (20 mmol) in DMF (10 ml) was added with stirring at room temperature to a solution prepared from potassium tert-butoxide (20 mmol) and 4-chlorophenol (20 mmol) in DMF (50 ml). The resultant mixture was stirred at 80° C. for 1 h, the solvent was then distilled off, the residue triturated with water, the residual material extracted with chloroform, the dried (MgSO$_4$) chloroform solution evaporated and the residue distilled; yield 3.65 g (64%), b.p. 135°-140° C./0.01 mmHg. $^1$H NMR (CDCl$_3$): δ 5.29 (CH$_2$), 6,6-7.4 (Ph's). MS [70 eV, m/Z (rel. int.)]; 2.84 (3,M), 159 (36), 157 (100), 111 (15), 105 (13), 75 (21).

The title compound:

Sulfuryl chloride (9.3 mmol) in dry dichloromethane (10 ml) was added to a solution of the above 1-(4-chlorophenylthio)methoxy-4-chlorobenzene (9.3 mmol) in dry dichloromethane (50 ml) over a period of 5 hours with stirring at room temperature. The reaction mixture was stirred for another 15 min at this temperature before a solution of cyclohexene (10 mmol) in dry dichloromethane (10 ml) was added with stirring over 5 min at 5° C. The mixture was stirred for another 20 min at room temperature, the solvent was then distilled off and the residue fractionally distilled; yield 1.40 g (85%), b.p. 40°-42° C./0.01 mmHg. The physical data have previously been reported (see Method A above).

The other product, the adduct between 4-chlorophenylsulphenyl chloride and cyclohexene had b.p. 118°-122° C./0.01 mmHg and was thus removed.

Preparation 4

1-Chloromethoxy-3-trifluoromethylbenzene (a) Synthesis of intermediate 1-(4-chlorophenylthio)-methoxy-3-trifluoromethylbenzene The synthesis was effected by reaction of 1-bromomethylthio-4-chlorobenzene and 3-trifluoromethylphenol in the same manner as described in preparation 3(b); yield 71%, b.p. 118°-122° C./0,01 mmHg. $^1$H NMR (CDCl$_3$); δ 5.13 (CH2), 7.1-7.5 (2×Ph), MS [70 eV 70, m/z (% rel. int)]: 318. (2,M), 159 (37), 157 (100), 145 (21) 121 (7), 108 (8), 75 (14)

(b) The title compound was prepared as described in Preparation 3 (b) by reaction of 1-(4-chlorophenylthio) methoxy-3-trifluoromethyl-benzene and sulfuryl chloride; yield 89%, b.p. 88°-90° C./15 mmHg. $^1$H NMR (CDCl$_3$): δ 5.82 (CH$_2$), 7.26 (Ph). MS [70 eV; m/z (% rel.int.)]: 212/210 (10/34,M); 191 (12), 175 (100), 145 (76), 133 (13), 127 (19), 114 (11), 113 (11).

Preparation 5

4-Chloro-1-(bromomethylsulfinyl)-benzene

90% m-Chloroperbenzoic acid (17 mmol) in chloroform (35 ml) solution was added dropwise with stirring over 1 h at 0° C. to a solution of 1-bromomethylsulfenyl-4-chlorobenzene (15 mmol) in chloroform (35 ml). The mixture was stirred at room temperature overnight, shaken with 1M K$_2$CO$_3$ aq., the dried (MgSO$_4$) chloroform solution evaporated and the solid residue recrystallized from CHCl$_3$: pet. ether; yield 3.20 g (84%), m.p. 100° C. $^1$H NMR (CDCl$_3$): δ 4.28 (CH$_2$), 7.53 (Ph). IR (KBr): 1040-1030 cm$^{-1}$ (SO).

Preparation 6

2,4-Dichloro-1-chloromethoxybenzene

Tris(triphenylphosphine) rhodium chloride (0.1 mmol) was added to freshly distilled 2,4-dichlorophenoxyacetyl chloride (28 mmol) and heated at 180° C. for 5 minutes before the mixture was distilled under vacuum to give 2,4-dichloro-1-chloromethoxybenzene (4.40 g). Yield: 75%, b.p. 57°-62° C./0.01 mm Hg (lit. b.p.: 137°-138° C./18 mm Hg see H. J. Barber, R. F. Fuller, M. B. Green and H. T. Zwartouw; J. Appl. Chem. 3, 266 (1953).

Preparation 7

4-Acetyl-1-chloromethoxybenzene

Method A

Tris(triphenylphosphine) rhodium chloride (0.02 mmol) was added to freshly distilled 4-acetylphenoxyacetyl chloride (3.8 mmol) and heated at 150° C. for 20 minutes before the mixture was distilled under vacuum to give 4-acetyl-1-chloromethoxybenzene (0.50 g). Yield: 71%, b.p. 89°–91° C./0.01 mm Hg.

Method B

1-Chloromethylthio-4-chlorobenzene (30 mmol) in DMF (15 ml) was added to a mixture of 4-acetylphenol (30 mmol) and potassium tert-butoxide (30 mmol) in DMF (55 ml). The mixture was stirred at 80° C. for 2 hours before the solvent was distilled off and the residue triturated with water, extracted with chloroform, dried (MgSO$_4$), evaporated and recrystallized from MeOH. Yield 6.0 g (68%), m.p. 56° C. The product (18 mmol) was dissolved in CH$_2$Cl$_2$ (50 ml) and SO$_2$Cl$_2$ (18 mmol) in CH$_2$Cl$_2$ (15 ml) was added with stirring at room temperature for 10 minutes. The mixture was stirred for 20 minutes before cyclohexene (19 mmol) in CH$_2$Cl$_2$ was added with stirring at 5° C. for 10 minutes. The mixture was stirred for 20 minutes at room temperature before the solvent was distilled off and the residue distilled under vacuum. Yield: 2.40 g (72%) b.p. 89°–91° C./0.01 mm Hg.

Preparation 8

α-Chloroethoxybenzene

Tris(triphenylphosphine) rhodium chloride (0.05 mmol) was added to freshly distilled 2-phenoxypropionyl chloride (13.5 mmol) and heated at 140° C. at 40 mm Hg whilst the product was being distilled off. The product was redistilled under vacuum to give α-chloroethoxybenzene. Yield: 0.80 g (38%), b.p. 80°–82° C./9 mm Hg.

Preparation 9

(1-Bromo-2-oxopropyl)oxybenzene

Phenoxy-2-propanone (0.10 mol), N-bromosuccinimide (0.10 mol) and a catalytic amount of 2,2'-azobis(2-methylpropionitrile) were stirred together in tetrachloromethane (100 ml) at 80° C. for 6½ hours. The solvent was distilled off and the residue distilled under vacuum to give (1-bromo-2-oxopropyl) oxybenzene. Yield: 10.4 g (45%), b.p. 66°–68° C./0.01 mm Hg. $^1$H NMR (CDCl$_3$, δ): 2.50 (s, CH$_3$) 6.40 (s, —CHBr—), 6.9–7.5 (5H, Ph).

Preparation 10

2-Chloromethylsulphenyl-1-methylimidazole

Triethylamine (40 mmol) was added to a mixture of 2-mercapto-1-methylimidazole (40 mmol) and bromochloromethane (0.8 mol). The mixture was stirred for 1 hour at room temperature, washed with water and the dried (MgSO$_4$) solution evaporated. Yield: 5.85 g (90%). $^1$H NMR (CDCl$_3$, δ): 3.77 (CH$_3$), 5.00 (CH$_2$), 6.7–7.2 (H-4 and H-5). The product was used in the succeeding step without further purification.

Preparation 11

5-Trifluoromethylpyrimidin-2-one (a) 2-Ethylthio-5-trifluoromethylpyrimidine Potassium tert-butoxide (8.9 mmol) was added to an ice-cooled solution of ethanethiol (8.9 mmol) in dimethoxyethane (40 ml) and the mixture stirred at room temperature for 10 min before 2-chloro-5-trifluoromethylpyrimidine (8.9 mmol) in dimethoxyethane (10 ml) was added. The resultant mixture was stirred at room temperature for 2 h and at 80° C. for 30 mins. The solvent was then removed at reduced pressure and the residue distilled; yield 1.40 g (76%), b.p. 110°–112° C./40 mmHg. $^1$H NMR (CDCl$_3$): δ 1.41 and 3.21 (Et), 8.65 (H-4 and H-6).

(b) 2-Ethylsulfonyl-5-trifluoromethylpyrimidine m-Chloroperbenzoic acid (12.0 mmol) was added to a solution of 2-ethylthio-5-trifluoromethyl-pyrimidine (5.5 mmol) in dichloromethane (30 ml) and the mixture stirred at room temperature for 24 h. The reaction mixture was then extracted with aqueous sodium bicarbonate, the organic layer dried (MgSO$_4$), the solvent distilled off and the residue crystallized from dichloromethane/pet. ether; yield 1.32 g (100%), m.p. 98° C. IR (KBr): 1320 and 1150 cm$^{-1}$ (SO$_2$) $^1$H NMR (CDCl$_3$): δ 1.44 and 3.61 (Et), 9.15 (H-4, H-6).

(c) 5-Trifluoromethylpyrimidin-2-one

2-Ethylsulfonyl-5-trifluoromethylpyrimidine (4.7 mmol) was added to 1M NaOH, the mixture stirred at 5° C. for 10 min, then at room temperature for 10 min and finally the pH was adjusted to 2 with HCl. After filtration the filtrate was evaporated, the residue dried and extracted with benzene, the benzene solution evaporated, the residue extracted with boiling ethyl acetate, (3×40 ml), and the ethyl acetate solution evaporated to yield the product; yield 0.50 g (67%). For final purification the product was sublimed at 110°–120° C./0,01 mmHg; m.p. 154° C., $^1$H NMR (DMSO-d$_6$): δ 8.50 (H-4, H-6), MS [70 eV; m/z (% rel. int.)]: 164 (99, M), 145 (21), 136 (100), 117 (25), 116 (16), 109 (11), 90 (28), 89 (40), 75 (35). IR (KBr): 1690 cm$^{-1}$ (CO).

Preparation 12

N-Chloromethylformanilide

4-Chloro-1-(chloromethylthio)benzene (21 mmol) was added to a mixture of formanilide (21 mmol) and potassium tert-butoxide (21 mmol) in DMF (200 ml). The mixture was stirred at 80° C. for 4 hours before the solvent was distilled off and the residue dissolved in ether and washed five times with water, and the dried (MgSO$_4$) solution evaporated. Yield: 5.37 g (92%), m.p. 67° C. (Pet. ether/ether). The product (17.8 mmol) was dissolved in CH$_2$Cl$_2$ (100 ml) and SO$_2$Cl$_2$ (17.8 mmol) in CH$_2$Cl$_2$ (25 ml) was added with stirring at 5° C. for 30 minutes. The mixture was stirred for 15 minutes before cyclohexene (19.3 mmol) in CH2Cl$_2$(25 ml) was added. The mixture was evaporated and the residue washed with hexane and dried. The product was used in the Example 28 without further purification. $^1$H NMR (CDCl$_3$,δ): 5.50 (s, —CH$_2$—), 7.34 (Ph), 8.33 (CHO).

Preparation 13

2-Chloromethoxynaphthalene

4-Chloro-1-(chloromethylthio)benzene (20mmol) in DMF (10 ml) was added to a mixture of 2-hydroxynaphthalene (20 mmol) and potassium tert-butoxide (20 mmol) in DMF (40 ml). The mixture was stirred at 80° C. for 2 hours before the solvent was distilled off and the residue triturated with water, extracted into ether and washed three times with water. The dried (MgSO$_4$) solution was evaporated and recrystallized from EtOH yield: 3.30g (57%). m.p. 70° C. The product (10.3 mmol) was dissolved in dry CH$_2$Cl$_2$ (30 ml) and SO$_2$Cl$_2$ (10.3 mmol) in dry CH$_2$Cl$_2$ (10 ml) was added with stirring at room temperature for 5 minutes. The mixture was stirred for 10 minutes before styrene (10.3 mmol) in dry CH$_2$Cl$_2$ (10 ml) was added with stirring at 5° C. for 10 minutes. The mixture was stirred for 20 minutes at room temperature before the solvent was distilled off and the residue distilled under vacuum. Yield: 1.50g (76%) b.p. 82°–95° C. 0.03 mmHg [see J. Appl. Chem. 3, 266(1953) b.p. 90°–110° C./0.15 mmHg].

Preparation 14

2-(Chloromethylthio)benzo[b]thiophene

Triethylamine (20 mmol) was added to a mixture of 2-mercaptobenzo[b]thiophene [see J. Chem.Soc. (C), 2731(1970)](20 mmol) and bromochloromethane (400 mmol). The mixture was stirred for 30 minutes at room temperature, washed with water and the dried (MgSO$_4$) solution evaporated. Yield: 4.08 g (95%). $^1$H-NMR (CDCl$_3$, δ): 4.88 (s,—CH$_2$—), 7.0–8.0 (m,5H,Ar). The product was used in Example 30 without further purification.

Preparation 15

1-Chloromethyl-5-chloropyrimidin-2-one

Sulphuryl chloride (3.0 mmol) in dry dichloromethane (10.0 ml) was added to 1-(4-chlorophenylsulphenyl)methyl-5-chloropyrimidin-2-one (see Example 2) (3.0 mmol) in dry dichlormethane 30.0 ml) at −30° C. for 3 mins. The mixture was stirred at −25° C. for 50 mins before cyclohexene (3.5 mmol) in dry dichloromethane (10 ml) was added. After stirring for 15 mins the mixture was filtered, evaporated and the residue washed three times with Pet. ether. Insoluble 1-chloromethyl-5-chloropyrimidin-2-one (0.45g), 84% was used in Example 31 without further purification.

Preparation 16

N-Chloromethyl acetanilide

4-Chloro-1-(chloromethylthio)benzene (30 mmol) was added to a mixture of acetanilide (30 mmol) and potassium tert-butoxide (30 mmol) in DMF (75 ml). The mixture was stirred at 80° C. for 2 hours before the solvent was distilled off, the residue dissolved in chloroform and washed three times with water. The dried solution (MgSO$_4$) was evaporated and the residue dissolved in ether. Remaining acetanilide was precipitated by adding Pet. ether and the solution evaporated. Yield 3.0 g. (43%). The crude product (13 mmol) was dissolved in CH$_2$Cl$_2$ (40 ml) and SO$_2$Cl$_2$ (13 mmol) in CH2Cl$_2$ (10 ml) was added with stirring at 5° C. over 5 minutes. The mixture was stirred for 10 minutes before cyclohexene (14 mmol in CH$_2$Cl$_2$ (10 ml) was added. After stirring for 10 minutes at 5° C. the mixture was evaporated and the residue washed with Pet.ether and dried. Yield 0.70 g (29%). The product was used in Example 32 without purification. $^1$H NMR (CDCl$_3$, δ): 1.92 (CH$_3$), 5.50 (—SCH$_2$), 7.1–7.7 (Ph).

Preparation 17

4-(Chloromethylthio) benzyl alcohol

4-Mercaptobenzyl alcohol (see J.Chem.Soc 1963 p 1947) (5.0 mmol) was dissolved in bromochloromethane (100 mmol) and triethylamine (5 mmol) added dropwise. The resultant mixture was stirred for 1 hour at room temperature, washed with water and the dried (MgSO$_4$) organic solution evaporated to leave the product. Yield 0.94 g (95%) $^1$H NMR (CDCl$_3$, δ): 2.03 (OH), 4.65 (CH$_2$O), 4.90 (CH$_2$S), 7.1–7.4 (Ph). The product needed no further purification for use in Example 33.

EXAMPLE 1

1-(4-Chlorophenoxy)methyl-5-chloropyrimidin-2-one

Method A

Potassium tert-butoxide (2.0 mmol) in DMF (5 ml) was added to a solution of 5-chloropyrimidin-2-one (2.0 mmol) in DMF (20 ml). The mixture was stirred at room temperature for 10 min before 1-chloromethoxy-4-chlorobenzene (see Preparation 3) (2.2 mmol) was added. The resultant mixture was stirred at room temperature for 30 min, and at 60° C. for 30 min, the solvent removed at reduced pressure and the residual material triturated with water and dried. The product was a mixture of the N- and O-alkylated isomers in the ratio 2:3; yield 0.40 g (74%). The isomers were separated by their different solubilities in acetone, the O-isomer being the more soluble. Physical data are given below:

Method B

A mixture of 5-chloropyrimidin-2-one (6 mmol) and triethylamine, (6 mmol) in dichloromethane (60 ml) was stirred together until all the solid material had dissolved, before a solution of 1-chloromethoxy-4-chlorobenzene (6 mmol) in dichloromethane (10 ml) was added with stirring at 0° C. After the addition, the mixture was left at room temperature overnight, the solvent distilled off and the residue triturated with water and dried; yield 1.50 g (90%) of the N- and O-isomers in the ratio 4:1 ($^1$H NMR). The isomers were separated as above. The title compound, the N-isomer, had m.p. 163° C. (CHCl$_3$/pet. ether). (Found: C49.23; H2.95. Calc. for C$_{11}$H$_8$Cl$_2$O$_2$: C48.73; H2.98) $^1$H NMR (DMSO-d$_6$) δ 7.78 (CH$_2$), 7.0–7.4 (Ph), 8.64 and 8.71 (H-4, H-6 d, J 4

Hz). IR (KBr): 1670 cm$^{-1}$ (CO). MS (70 eV; m/z (% rel. int.)): 274/270 (1/6/9, M), 145 (62), 113 (100).

EXAMPLE 2

1-(4-Chlorophenylsulfenyl)methyl-5-chloropyrimidin-2-one

Potassium tert-butoxide (40 mmol) in DMF (25 ml) was added to a solution of 5-chloropyrimidin-2-one hydrochloride (20 mmol) in DMF (125 ml). The mixture was stirred at room temperature for 15 min before 1-bromomethylsulfenyl-4-chlorobenzene [see U.S. Pat. No. 2,827,492; Chem. Abstract 52 Pl 6296 d (1958)](25 mmol) was added. The resultant mixture was stirred at room temperature at 60° C. for 3h, the solvent removed at reduced pressure and the residue triturated with water and dried. The residual product was a mixture of the N- and O-alkylated isomers in the ratio 3:1 ($^1$H NMR); yield 4.2 g (73%). The isomers were separated by their different solubilities in acetone, the less polar O-isomer being the more soluble isomer. The title compound, the N- isomer had m.p. 191° C. (acetone). (Found C45.90; H2.78. Calc. for $C_{11}H_8Cl_2N_2OS$: C46.00; H2.81) $^1$H NMR (CDCl$_3$): δ 5.25 (CH2), 7.35 (Ph, s), 8.20 and 8.50 (H-4, H-6, d, J 4 Hz). IR (KBr): 1660 cm$^{-1}$ (CO). MS (70 eV; m/z (% rel. int)): 286 (4, M), 157 (11), 156 (11), 145 (33), 143 (100), 116 (27).

EXAMPLE 3

1(4-Chlorophenylsulfinyl)methyl-5-chloropyrimidin-2-one

Potassium tert-butoxide (4 mmol) in DMF (10 ml) was added to a solution of 5-chloropyrimidin-2-one (4 mmol) in DMF (40 ml). The mixture was stirred at room temperature for 10 min before 1-bromomethyl-sulfinyl-4-chlorobenzene (see Preparation 5) (4 mmol) was added. The resultant mixture was stirred at 60° C. for 2 days, the solvent distilled off at reduced pressure, the residue triturated with water, the insoluble material dried and washed with a little chloroform before recrystallization from DMSO; the crystalline material was also washed with a little methanol and finally with water; yield 0.30 g (25%), m.p. 262° C. (Found: C43.63; H2.68. Calc. for $C_{11}H_8Cl_2N_2O_2S$: C43.59; H2.67) $^1$H NMR (DMSO-d$_6$); δ 5.12 (CH2), 7.60 (Ph, b.s.), 8.19 and 8.62 (H-4, H-6, d, J 4 Hz). IR (KBr): 1660 (CO), 1060 cm-$^1$ (SO). MS (70 eV; m/e (rel. int. %): 302 (0.5, M), 159 (6), 145 (33), 143 (100).

EXAMPLE 4

1-(N-phenyl-N-ethoxycarbonylamino)methyl-5-chloropyrimidin-2-one

Potassium tert-butoxide (40 mmol) in DMF (25 ml) was added to a solution of 5-chloropyrimidin-2-one hydrochloride (20 mmol) in DMF (100 ml). The mixture was stirred at room temperature for 15 min before ethyl N-chloromethyl-N-chloromethyl-N-phenyl-carbamate (see German Offenlegungsschrift No. 2,119,518) (23 mmol) was added. The resultant mixture was stirred at 60° C. for 3h, the solvent distilled off at reduced pressure, the residue triturated with water and the insoluble material crystallized from methanol; yield 4.0 g (65%), m. p. 174° C. (Found: C54.60; H4.59. Calc. for $C_{14}H_{14}ClN_3O_3$: C54.69 H4.59) $^1$H NMR (CDCl$_3$): δ 1.18 and 4.20 (Et), 5.62 (CH2), 7.0–7.4 (Ph), 8.10 and 8.46 (H-4, H-6, d, J 4 Hz). IR (KBr): 1720 cm$^{-1}$ (CO ester), 1680 cm$^{-1}$ (CO pyr). MS (70 eV; m/z (% rel. int.)): 307 (7, M), 178 (71), 143 (15), 134 (25), 106 (100), 78 (25).

EXAMPLE 5

1-(5-Chloropyrimidin-2-sulfenyl)methyl-5-chloropyrimidin-2-one 2-(Iodomethyl)thio-5-chloropyrimidine (see European patent application No. 81300098.1) (15.6 mmol) in DMF (20 ml) was added to the potassium salt of 5-chloro-pyrimidin-2-one (15.0 mmol) in DMF (60 ml). The mixture was stirred at room temperature for 8 h before the solvent was distilled off. The residue was triturated with water and the insoluble N- and O-alkylated isomers separated by fractional crystallization from acetone; 2-(5-chloropyrimidin-2-oxymethyl)-thio-5-chloropyrimidine was the more soluble isomer; yield 36%, m.p. 128° C. (MeOH). $^1$H NMR (CDCl$_3$): δ 6.15 (CH2), 8.48 (2 H in pyrimidine), 8.51 (2 H in pyrimidine).

The less soluble isomer in acetone solution was 1-(5-chloropyrimidin-2-sulfenyl)methyl-5-chloropyrimidin-2-one; yield 64%, m.p. 210° C. (acetone). (Found: C37.59; H2.07. Calc. for $C_9H_6Cl_2N_4OS$; C37.38, H2.10). $^1$H NMR (CDCl$_3$) δ 5.56 (CH$_2$—), 8.29 and 8.57 (H-4, H-6, J 3 Hz), 8.62 (H'-4, H'-6). IR (KBr): 1670 cm$^{-1}$ (CO) MS (70 eV; m/e (% rel. int)); 288 (20, M) 159 (23), 149 (40), 147 (100), 143 (73).

EXAMPLE 6

1-(Phenoxy)methyl-5-chloropyrimidin-2-one

5-Chloropyrimidin-2-one (5 mmol) and triethylamine (5 mmol) were stirred together in dichloromethane (50 ml). When all the solid had dissolved a solution of chloromethoxybenzene (see Preparation 2) (5 mmol) in dichloromethane (25 ml) was added with stirring at room temperature. The resultant mixture was stirred for 24 h at this temperature before the solvent was distilled off. The residue was triturated with water (30 ml), extracted into chloroform (3×20 ml), and the dried (MgSO$_4$) solution evaporated to yield a mixture of the title compound and the O-alkylated isomer in the ratio 3:1; yield 7.00 g (85%). The N-isomer was separated by column chromatography on silica gel; m.p. 146° C. $^1$H NMR (CDCl$_3$): δ 5.92 (CH$_2$), 6.8–7.4 (Ph), 7.80 and 8.43 (H-4 and H-6, respectively, J 3 Hz). IR (KBr): 1660 cm$^{-1}$ (CO). MS (70 eV, m/z (% rel. int.)): 236 (7, M), 145 (32), 143 (100), 116 (31), 94 (6), 77 (18).

EXAMPLE 7

1-(4-Chlorophenoxy)methyl-5-bromopyrimidin-2-one

Method A

The title compound was prepared as described for the 5-chloro analogue in Example 1 by the addition of 1-chloromethoxy-4-chlorobenzene (see Preparation 3) (5 mmol) to a solution of 5-bromopyrimidin-2-one (5 mmol) and potassium tert-butoxide (5 mmol) in DMF (80 ml). The product 1.20 g (70%), consisted of the N- and O-isomers in the ratio 2:3. The O-isomer was removed from the product by extraction with acetone succeeded by recrystallization of the N-isomer from acetone; m.p. 200° C. (Found C42.31; H2.64 Calc. for $C_{11}H_8BrClN_2O_2$: C41.86; H2.56). $^1$H NMR (DMSO-d$_6$/CDCl$_3$) δ 5.81 (CH$_2$), 7.0–7.3 (Ph), 8.49 and 8.60 (H-4 and H-6, respectively, J 3 Hz). IR (KBr): 1660 cm$^{-1}$(CO). MS (70 eV, m/z (% rel. int.) 316/314 (6/5,M), 189 (96), 187 (100), 162 (16), 160 (17).

Method B

2-Trimethylsilyloxy-5-bromopyrimidine (6.7 mmol), [prepared by heating 5-bromopyrimidin-2-one in excess bis (trimethylsilylamine) until a clear solution was obtained followed by evaporation to leave the trimethylsilyl ether] and 1-chloromethoxy-4-chlorobenzene (see Preparation 3) (6.0 mmol) were heated together at 120° C. for 30 min. The mixture allowed to cool, chloroform (75 ml) added and the mixture heated under reflux for 10 min. The cold mixture was filtered, the filtrate evaporated and the residue triturated with ether; yield 0.70 g (37%). The physical properties were as described in the synthesis according to Method A.

EXAMPLE 8

1-(4-Chlorophenoxy)methyl-5-iodopyrimidin-2-one

The title compound was prepared in a manner similar to that described in Example 6, by adding a solution of 1-chloromethoxy-4-chlorobenzene (see Preparation 3) (10 mmol) in dichloromethane (10 ml) to a solution of 5-iodopyrimidin-2-one (10 mmol) and triethylamine (10 mmol) in dichloromethane (50 ml), and heating the resultant mixture under reflux for 3 h. The product, 2.05 g (56%), consisted of the N- and O-isomers in the ratio 4:1. The O-isomer was removed from the product by extraction with acetone and the remaining N-isomer was recrystallized from EtOAc; m.p. 216° C. (Found C36.64; H2.24 Calc. for $C_{11}H_8ClIN_2O_2$: C36.44; H2.23) $^1$H NMR (DMSO-d$_6$/CDCl$_3$); δ 5.85 (CH$_2$), 6.9–7.5 (Ph), 8.68 and 8.82 (H-4 and H-6, respectively, J 3 Hz). IR (KBr) 1650 cm$^{-1}$ (CO). MS (70 eV, m/z (% rel. int.)): 362 (37,M) 235 (100), 222 (6), 108 (22).

EXAMPLE 9

1-(2,4-Dichlorophenoxy)methyl-5-chloropyrimidin-2-one

The title compound was prepared in a manner similar to that described in Example 6 by the addition of a solution of 1-chloromethoxy-2,4-dichlorobenzene (see preparation 6) (5 mmol) in dichloromethane (25 ml) to a solution of 5-chloropyrimidin-2-one (5 mmol) and triethylamine (5 mmol) in dichloromethane (75 ml). The mixture was stirred at room temperature for 2 h and at 40° C. for 7 h before being worked up as above; yield 1.30 g (80%), isomer ratio 3:1. The title compound crystallized from DMSO: m.p. 170° C. $^1$H NMR (TFA): δ 6.10 (CH$_2$),, 6.9–7.4 (Ph), 9.0–9.2 (H-4, H-6). IR (KBr): 1680 cm$^{-1}$ (CO). MS (70 eV, m/z (% rel. int.)): 304 (1,M), 162 (3), 145 (35), 143 (100), 116 (28).

EXAMPLE 10

1-(4-Tolyloxy)methyl-5-chloropyrimidin-2-one

The title compound was prepared by adding a solution of 4-(chloromethoxy)toluene (see J.Appl. Chem. 3, 266(1953)) (10 mmol) in dichloromethane (10 ml) to a solution of 5-chloropyrimidin-2-one hydrochloride (10 mmol) and triethylamine (20 mmol) in dichloromethane (50 ml). The mixture was stirred at room temperature for 2 days. The product, 1.90 g (76%), consisted of the N- and O-isomers in the ratio 3:1. The N-isomer was isolated by its lower solubility in ether; m.p. 186° C. (acetone). (Found: C57.59; H4.65 Calc. for $C_{12}H_{11}ClN_2O_2$: C57.49; H4.43) $^1$H NMR (CDCl$_3$): δ 2.25 (Me), 5.74 (CH$_2$), 6.8–7.3 (Ph), 7.80 and 8.50 (H-4 and H-6, respectively, J 3 Hz). IR (KBr): 1680 cm$^{-1}$ (CO). MS [70 eV, m/z% rel. int.)[: 250 (7,M), 145 (31), 143 (100), 116 (28).

EXAMPLE 11

1-(4-Acetylphenoxy)methyl-5-chloropyrimidin-2-one

The title compound was prepared in a manner similar to that described in Example 6 by adding a solution of 4-acetyl-1-(chloromethoxy)benzene [see Preparation 7] (2.2 mmol) in dichloromethane (5 ml) to a solution of 5-chloropyrimidin-2-one hydrochloride (2.2 mmol) and triethylamine (4.4 mmol) in dichloromethane (20 ml). The product was the desired N-alkylated isomer; yield: 0.60 g (100%), m.p. 182° C. (acetone). (Found C56.38 H4.15 Calc. for $C_{13}H_{11}ClN_2O_3$: C56.02; H3.99) $^1$H NMR (CDCl$_3$) δ 2.50 (Me), 5.82 (CH$_2$), 7.0 and 7.8 (H-4 and H-6, respectively, J 3 Hz). [70 eV, m/z, % rel. int.)]: 278 (7,M), 145 (31), 143 (100), 136 (18), 121 (33), 116 (22), 93 (15).

EXAMPLE 12

1-α-Phenoxyethyl-5-chloropyrimidin-2-one

The title compound was prepared in a manner similar to that described in Example 6 by adding a solution of α-chloroethoxybenzene [see Preparation 8] (4.5 mmol) in dichloromethane (5 ml) to a solution from 5-chloropyrimidin-2-one hydrochloride (4.5 mmol) in dichloromethane (15 ml) at 5° C., and the mixture was stirred at room temperature for 2 h before being worked up. The product was a mixture of the desired N-isomer and the O-isomer in the ratio 3:2; yield 0.85 g (76%). The isomers were separated by chromatography on silica gel using chloroform as above; m.p. 92° C. (CH$_2$Cl$_2$/Pet.ether). (Found: C58.02; H 4.51 Calc. for $C_{12}H_{11}ClN_2O_2$: C57.49; H4.43) $^1$H NMR (CDCl$_3$): δ 1.72 (Me, d, J 5 Hz), 6.47–7.3 (Ph,H-δ), 7.79 and 8.40 (H-4 and H-6, respectively, J 3 Hz). IR (KBr): 1665 cm$^{-1}$ (CO). MS [70 eV, m/z (% rel. int.)]: 250 (1,M), 159 (30)), 157 (100), 121 (23), 77 (30), 65 (17).

EXAMPLE 13

1-[Acetyl(phenoxy)]methyl-5-chloropyrimidin-2-one

The title compound was prepared in a manner similar to that described in Example 6, by adding a solution of (1-bromo-2-oxopropyl)oxybenzene [see preparation 9] (39 mmol) in dichloromethane (25 ml) to a solution from 5-chloropyrimidin-2-one hydrochloride (39 mmol) and triethylamine (78 mmol) in dichloromethane (275 ml) at 5° C. The product, 10.0 g (92%), was a mixture of the N- and O-isomers in the ratio 2:1; the isomers were separated by chromatography as above. The N-isomer was a non-crystalline material. $^1$H NMR (CDCl$_3$) δ 2.50 (MeCO), 6.8 ; 7.3 (Ph,m, H-α), 7.55 and 8.46 (H-4 and H-6, respectively, J 3 Hz). IR (KBr): 1740 cm$^{-1}$(CH$_3$CO), 1670 cm$^{-1}$(CO).

EXAMPLE 14

1-(3-Tolylsulfenyl)methyl-5-chloropyrimidin-2-one

Potassium tert-butoxide (20 mmol) in DMF (12 ml) was added to a solution of 5-chloro-pyrimidin-2-one hydrochloride (10 mmol) in DMF (60 ml). After stirring for 13 min, a solution of 3-chloromethylthiotoluene (10 mmol) in DMF (12 ml) was added. The resultant mixture was stirred at 60° C. for 3 h, the solvent distilled off at reduced pressure and the residue triturated and washed well with water before drying. The product was the N- and O-alkylated isomers in the ratio 7:5;

yield: 1.71 g (64%). The N-isomer was isolated by its low solubility in ether in which the O-isomer is readily soluble; m.p. 134° C. (isoPrOH/EtOH). (Found C53.73; H4.25. Calc. for $C_{12}H_{11}ClN_2OS$: C54.03; H4.16) $^1$H NMR (DMSO-d$_6$): δ 2.27 (Me), 5.22 (CH$_2$), 7.17 (Ph). 8.00 and 8.56 (H-4 and H-6, J 4 Hz). IR (KBr): 1660 cm$^{-1}$ (CO). MS [70 eV, m/z (% rel. int.)]: 266/268 (6/2,M) 143/145 (100/32). MS [70 eV, m/z (% rel. int.)]: 266/268 (11/4,M, 137 (100).

EXAMPLE 15

1-(3-Tolylsulfenyl)methyl-5-bromopyrimidin-2-one

The title compound was prepared from 5-bromopyrimidin-2-one hydrochloride (10 mmol) in a manner similar to that described in Example 14 for the 5-chloro analogue. The yield was 2.08 g (67%) of the N- and O-isomers in the ratio 3:2. The N-isomer was isolated by its low solubility in methanol in which the O-isomer is readily soluble, m.p. 164° C. (MeOH). (Found C46.46; H3.62. Calc. for $C_{12}H_{11}Br\ N_2OS$: C46.32; H3.56). $^1$H NMR (CDCl$_3$) δ 2.30 (Me), 5.23 (CH$_2$), 7.2 (Ph), 8.03 and 8.57 (H-4 and H-6, respectively, J 4 Hz). IR (KBr): 1660 cm$^{-1}$(CO). MS [70 eV, m/z (% rel. int.)] 310/312 (4/4, M) 187/189 (100/95).

EXAMPLE 16

1-(4-Fluorophenylsulfenyl)methyl-5-chloropyrimidin-2-one

The title compound was prepared from 5-chloropyrimidin-2-one hydrochloride (10 mmol) and 4-fluoro-1-(chloromethylthio)benzene (10 mmol) in a manner similar to that described in Example 2. The reaction time was 2¾ h. Yield: 1.60 g (59%) of the N- and O-isomers in the ratio 2:1. The N-isomer was isolated by its lower solubility in methanol; m.p. 179° C. (MeOH/H$_2$O/ isoPrOH). $^1$H NMR (DMSO-d$_6$): δ 5.25 (CH$_2$), 6.9–7.7 (Ph), 8.07 and 8.53 (H-4 and H-6, J 4 Hz). IR (KBr): 1660 cm$^{-1}$(CO). (Found: C49.80; H2.54. Calc. for $C_{11}H_8ClFN_2OS$: C48.81; H2.98). MS [70 eV, m/z (% rel. int.]): 270/272 (4/2,M), 143/145 (100/32).

EXAMPLE 17

1-(4-Fluorophenylsulfenyl)methyl-5-bromopyrimidin-2-one

The title compound was prepared from 5-bromopyrimidin-2-one hydrobromide (10 mmol) in a manner similar to that described in Example 16 for the 5-chloro analogue. The reaction time was 3 h. Yield: 2.21 g (70%) of the N- and O-isomer in the ratio 9:5. The O-isomer was extracted from the mixture with methanol in which the N-isomer is less soluble. The remaining N-isomer, the title compound, was recrystallized from MeOH/HOAc; m.p. 206° C. (Found: C42.06; H2.62. Calc. for $C_{11}H_8\ BrFN_2OS$: C41.92; H2.56) NMR (TFA): δ 5.47 (CH$_2$), 7.0–7.7 (Ph), 8.30 and 8.90 (H-4 and H-6, respectively, J 3 Hz). IR (KBr) 1660 cm$^{-1}$(CO). MS [70 eV, m/z (% rel. int.)]: 314/316 (5/6,M), 187/189 (100/98).

EXAMPLE 18

1-(4-Methoxyphenylsulphenyl)methyl-5-chloropyrimidin-2-one

The title compound was prepared from 5-chloropyrimidin-2-one hydrochloride (10 mmol) and 1-chloroethylthio-4-methoxy benzene [see Preparation 1](10 mmol) in a manner similar to that described in Example 2. The reaction time was 2 h. Yield: 2.46 g (87%) of the N- and O-isomers in the ratio 7:5. The N-isomer was isolated by its lower solubility in methanol; m.p. 140° C. (MeOH). (Found C41.23; H4.00 Calc. for $C_{12}H_{11}ClN_2O_2S$: C50.97; H3.93) $^1$H NMR (DMSO-d6) 3.77 (OMe), 5.12 (CH2), 6.8–7.4 (Ph), 7.90 and 8.56 (H-4 and H-6, respectively, J 4 Hz). IR (KBr): 1660 cm$^{-1}$ (CO. MS (70 eV, m/z % rel. int.)]: 282/284 (5/2,M), 143/145 (100/33).

EXAMPLE 19

1-(4-Nitrophenylsulfenyl)methyl-5-chloropyrimidin-2-one

The title compound was prepared from 5-chloropyrimidin-2-one hydrochloride (10 mmol) and 4-nitro-1-(chloromethylthio)benzene (10 mmol) in a manner similar to that described in Example 2. The reaction time was 3½ h. Yield: 1.79 g (60%) of the N- and O-isomers in the ratio 5:2. The O-isomer was extracted from the mixture with chloroform, and the remaining N-isomer, the title compound, was recrystallized from MeOH/HOAc; m.p. 165° C. (Found C44.64; H3.03. Calc. for $C_{11}H_8ClN_3O_3S$: C44.37; H2.71) $^1$H NMR (DMSO-d$_6$): δ 5.50 (CH$_2$), 7.4–8.3 (Ph), 8.51 (H-4 and H-6, s). IR (KBr): 1660 cm$^{-1}$(CO). MS [70 eV, m/z (% rel. int.)]: 297/299 (5/2,M), 143/145 (100/31).

EXAMPLE 20

1-(5-Chloropyrimidin-2-on-1-yl)methyl-5-chloropyrimidin-2-one

A mixture of 5-chloropyrimidin-2-one hydrochloride (18 mmol), triethylamine (36 mmol) and bromochloromethane (30 ml) was heated with stirring under reflux for 3 h. The precipitate from the cold reaction mixture was collected, washed with water, and acetone and finally with ether. There remained 1.25 g (51%) of the title compound, m.p. 260° C. (Found C39.53; H2.12. Calc. for $C_8H_6Cl_2N_4O_2$: C39.58; H2.22) $^1$H NMR (TFA) δ 6.32 (CH$_2$), 8.7–9.4 (H-4 and H-6). IR (KBr): 1670 cm$^{-1}$ (CO). MS (70 eV, m/z (% rel. int.)]: 272 (8,M), 145 (33), 144 (29), 143 (100).

EXAMPLE 21

1-(1-Methylimidazol-2-sulfenyl)methyl-5-chloropyrimidin-2-one

2-Chloromethylsulfenyl-1-methylimidazole [see Preparation 10] (10 mmol) in DMF (12 ml) was added to a mixture of 5-chloropyrimidin-2-one hydrochloride (10 mmol) and potassium tert-butoxide (20 mmol) in DMF (72 ml). The mixture was stirred at 60° C. for 5½ hours before the product was distilled off and the residue washed with water and ether. The product was oily. $^1$H HMR (DMSO d$_6$, δ): 3.57 (CH$_3$), 5.27 (—CH$_2$—), 6.95 - 7.22 (imidazole), 8.19 (H-4, d, j 4 Hz), 8.54 (H-6, d, J 4 Hz).

EXAMPLE 22

1-(Phenoxy)methyl-4,6-dimethyl-5-bromopyrimidin-2-one

A mixture of 4,6-dimethyl-5-bromopyrimidin-2-one (4.7 mmol) and triethylamine (4.7 mmol) in dichloromethane (60 ml) was heated at 40° C. for dissolution. The solution was then cooled to room temperature and (chloromethoxy)benzene [see Preparation 2] (4.7 mmol) in dichloromethane (15 ml) was added. The resultant mixture was stirred at room temperature for 1½ h, the solvent distilled off, the mixture triturated with water, the remaining solid extracted with chloroform, the dried (MgSO$_4$) chloroform solution evaporated, the residue triturated with a little ether, the residue redissolved in chloroform and the solution chromatographed on a column of alumina, activity III, using chloroform, Yield 0,35 g (24%), m.p. 120° C. (CCl$_4$) (Found C50.32; H4.15. Calc. for C$_{13}$H$_{13}$BrN$_2$O$_2$: C50.50; H4.25) $^1$H NMR (CDCl$_3$): δ 2.50 and 2.68 (4-Me and 6-Me), 6.03 (CH$_2$), 6.8–7.4 (Ph), MS [70 eV, m/z (% rel. int)]. 310/308 (6/7,M), 217(97), 215(100), 174(15), 172(12), 136(20), 135(19), 108(23) 94(19).

EXAMPLE 23

1-(3-Trifluoromethylphenoxy)methyl-5-chloropyrimidin-2-one

A solution of 1-chloromethoxy-3-trifluoromethylbenzene [see Preparation 4] (7 mmol) in dichloromethane (10 ml) was added to a solution of 5-chloropyrimidin-2-one hydrochloride (70 mmol) in dichloromethane (30 ml) and the mixture stirred at room temperature for 18 h. The solvent was then distilled off, the mixture triturated with water, the residual solid extracted with chloroform and the dried (MgSO$_4$) chloroform solution evaporated; yield 1.88 g (94%). The product was a mixture of the N- and O-isomer in the ratio 3:1. The isomers were separated by the difference in their solutilities in tetrachloromethane, the O-isomer being the more solunble. The title compound, the N-isomer was isolated in a non-crystalline form. $^1$H NMR (CDCl$_3$) δ 5.82 (CH$_2$), 7.1–7.3 (Ph), 7.85 (H-4, J$_{4,6}$ 3 Hz), 8.45 (H-6).

EXAMPLE 24

1-(3-Methylphenylthio)methyl-5-fluoropyrimidin-2-one 3-(Chloromethylthio)toluene (6.5 mmol) was added to a solution of 5-fluoropyrimidin-2-one (6.5 mmol) and triethylamine (6.5 mmol) in dichloromethane (75 ml) and the resultant mixture heated under reflux for 2 days. The solvent was then distilled off, the residue triturated with water and the residual material extracted with CCl$_4$. Evaporation of the extracts and crystallisation of the residue from ethyl acetate gave the pure product; 0.40 g (25%), m.p. 124° C. (Found: C57.42; H4.63. Calc. for C$_{12}$H$_{11}$FN$_2$OS: C57.59; H4.43) $^1$H NMR (DMSO d$_6$); δ 2.28 (Me), 5.17(CH$_2$), 7.2 (Ph), 8.05 (H-4), 8.70 (H-6). IR (KBr): 1670 cm$^{-1}$ (CO), MS [70 eV, m/z (% rel. int.)]: 250 (8,M), 137(11), 136)36), 135(10), 128(7), 127(100), 100(34), 91(9).

EXAMPLE 25

1-(4-Methyloxycarbonylphenylthio)methyl-5-iodopyrimidin-2-one

A solution of methyl4-(chloromethylthio)benzoate [The methyl 4-(chloromethylthio)benzoate reagent was made in the conventional manner as previously described for its analogues in Preparations 1 and 4 by chloromethylation of methyl 4-mercaptobenzoate; yield 92%](8.2 mmol) in DMF (10 ml) was added dropwise to a stirred suspension of the sodium salt of 5-iodopyrimidin-2-one (8.2 mmol) in DMF (50 ml) and the final mixture heated at 60° C. for 3h. The solvent was then distilled off, the residue triturated with water and with a little ether. The product was a mixture of the N- and O-isomers in the ratio 4:1; yield 1.50 g (45%). The title compound, the N-isomer, was obtained after fractional crystallisation from ethyl acetate and methanol, m.p. 210° C. NMR (TFA); δ 4.09 (Me), 5.60 (CH$_2$), 7.4–8.2 (Ph), 8.67 (H-4, J$_{4,6}$ 3Hz) 8.87 (H-6). IR (KBr): 1640 (CO), 1710 cm$^{-1}$ (CO-ester). MS [70 eV, m/z (% rel. int.)].

EXAMPLE 26

1-(4-Chlorophenoxy)methyl-5-trifluoromethylpyrimidin-2-one

A solution of 1-chloromethoxy-4-chloro-benzene [see Preparation 11](0.35 mmol) in dichloromethane (1 ml) was added with stirring at room temperature to a solution prepared from 5-trifluoromethyl-pyrimidin-2-one (0.33 mmol) and triethylamine (0.33 mmol) in dichloromethane (5 ml). The mixture was stirred at room temperature for 24 h and then it was stirred at 70° C. for 30 min, the solvent was then distilled off, the residue triturated with water, the residual material extracted with chloroform and the dried (MgSO$_4$) chloroform solution evaporated to yield the product, 60 mg (62%), as a mixture of the N- and O-isomers in the ratio 5:1. The isomers were separated by their different solubilities in ether, the O-isomer being the more soluble. The title compound, the N-isomer had m.p. 98° C. (Found C46.78; H2.88. Calc. for C$_{12}$H$_8$ClF$_3$N$_2$O$_3$: C47.30; H2.65) $^1$H NMR (CDCl$_3$); δ 5.85 (CH$_2$), 6.8–7.4 (Ph), 8.15 (H-4, J$_{4,6}$3 Hz) 8.76 (H-6) MS [70 eV; m/z (% rel. int.)]; 177 (100), 150(10), 75(5), IR (KBr); 1690 cm$^{-1}$ (CO).

EXAMPLE 27

1-α-(4-chlorophenylsulphenyl)benzyl-5-chloropyrimidin-2-one

5-Chloropyrimidin-2-one hydrochloride (10 mmol) and triethylamine (20 mmol) were stirred together in CH$_2$Cl$_2$ (50 ml). When all the solid had dissolved there was added a solution of 4-chloro-1-(α-chlorobenzylthio)-benzene (10 mmol) in CH$_2$Cl$_2$ (20 ml) with stirring at room temperature for 15 minutes. The mixture was stirred at room temperature for 6 hours and at 40° C. for 20 minutes before the solvent was distilled off. The residue was triturated with water, extracted into chloroform, dried (MgSO$_4$) and evaporated to yield a mixture of the title compound and the O-alkylated isomer in the ratio 4:3. Yield 3.16 g (96%). The O-isomer was removed from the product by extraction with acetone succeeded by recrystallization of the N-isomer from CH$_2$Cl$_2$/Pet. ether, m. p. 144° C. $^1$H NMR (acetone-d$_6$+DMSO-d$_6$, δ): 7.0–7.7 (10 H, Ar, —CH), 8.42 (1H, d, J 3 Hz, H-4), 8.72 (1 H, d, J 3Hz, H-6). IR (KBr, cm$^{-1}$): 1660 (CO).

EXAMPLE 28

1-(N-Formyl-N-phenylamino)methyl-5-chloropyrimidin-2-one

5-Chloropyrimidin-2-one hydrochloride (3.0 mmol) and triethylamine (6 mmol) were stirred together in CH$_2$Cl$_2$ (50 ml) for 15 minutes before a solution of N-chloromethylformanilide (see Prepartion 12) (3 mmol) in CH$_2$Cl$_2$ was added. The mixture was stirred at 40° C. for 18 hours before the solvent was distilled off. The residue was washed with water and ether. Yield: 0.79 g (50%), m. p. 200° C. (EtOH). $^1$H NMR (DMSO-d$_6$, δ): 5.68 (s, CH$_2$), 7.32 (Ph), 8.05–8.65 (CHO, H-4 and H-6). IR (KBr, cm$^{-1}$): 1660 (CO), 1680 (CO). MS (70 eV, m/e (% rel. int.)): 263 (M$^+$, 1), 143 (7), 134 (41), 116 (6), 107 (6), 106 (100), 105 (57), 104 (10), 79 (10), 78 (7), 77 (41), 52 (11), 51 (20).

EXAMPLE 29

1-(2-Naphthoxy)methyl-5-chloropyrimidin-2-one

5-Chloropyrimidine-2-one hydrochloride (5 mmol) and triethylamine were stirred together in $CH_2Cl_2$ (30 ml). When all the solid had dissolved there was added a solution of 2-chloromethoxynaphthalene [see Preparation 13] (5 mmol) in $CH_2Cl_2$ (10 ml) with stirring at room temperature for 5 minutes. The mixture was stirred at room temperature for 24 hours before the solvent was distilled off. The residue was triturated with water, extracted into $CHCl_3$, dried ($MgSO_4$) and evaporated to give a mixture of the tite compound and the O-alkylated isomer in the ratio 4:1. Yield 1.27 g (86%). The O-isomer was removed from the product by extraction with ether followed by recrystallization of the N-isomer from acetone m.p. 168° C. $^1H$ NMR ($CDCl_3\delta$): 5.85 (s, $CH_2$), 7.10–8.1 (m, 8H. Ar+H-4), 8.48 (H-6, $d_7=4$ Hz) IR (KBr, $cm^{-1}$): 1675 (CO).

EXAMPLE 30

1-(Benzo[b]thienyl-2-sulphenyl)methyl-5-chloropyrimidin-2-one

5-Chloropyrimidin-2-one hydrochloride (5 mmol) and triethylamine (16 mmol) were stirred together in $CH_2Cl_2$ (75 ml). When all the solid had dissolved there was added a solution of 2-chloromethylthiobenzo[b]thiophene [see Preparation 14] (8 mmol) in $CH_2Cl_2$. The mixture was stirred at 40° C. for 36 hours and the cooled solution washed with water, dried ($MgSO_4$) and evaporated. The residue was washed with ether to give the title compound. Yield 0.50 g (20%) m.p. 186° C. $^1H$ NMR ($CDCl_3$): $\delta$ 5.05 (s, —$CH_2$—), 7.26 (m. Ph) 7.5–7.8 (m, 2H): 8.41 (H-6,$d_7=3$ Hz) IR (KBr. $cm^{-1}$): 1660 (CO).

EXAMPLE 31

1-(3-Tolylsulphenyl)methyl-5-chloropyrimidin-2-one

1-Chloromethyl-5-chloropyrimidin-2-one (see Preparation 15)

(1.0 mmol) was added to a mixture of m-thiocresol (1.0 mmol) and triethylamine (1.0 mmol). The mixture was stirred at room temperature for 20 mins and at 40° C. for 20 mins before the solvent was distilled off and the residue triturated with water, extracted into chloroform, dried ($MgSO_4$) and evaporated. The residue was washed with cold acetone (1 ml). The insoluble product was identical with an authentic sample prepared as described in Example 14. Yield: 60 mg, 22%.

EXAMPLE 32

1-(N-Acetyl-N-phenylamino)methyl-5-chloropyrimidin-2-one

5-Chloropyrimidin-2-one hydrochloride (3.8 mmol) and triethylamine (7.6 mmol) was stirred together in $CH_2Cl_2$ (30 ml) for 10 minutes before a solution of N-chloromethyl acetanilide (see Preparation 16) (3.8 mmol) in $CH_2Cl_2$ (5 ml) was added. The mixture was stirred at 40° C. for 2 hours before the solvent was distilled off and the residue washed with water and ether. Yield 0.3 g, (28%) M.p. 150°–155° C. (decomp) ($CH_2Cl_2$/ pet. ether) $^1H$ NMR ($CDCl_3$, $\delta$): 1.90 ($CH_3$), 5.60 ($CH_2$), 6.9–7.4 (Ph), 8.18 and 8.42 (H-4, H-6, J3 Hz). IR (KBr) 1670–1680 $cm^{-1}$ (CO).

EXAMPLE 33

1-(4-Hydroxymethylphenylthiomethyl)-5-chloropyrimidin-2-one 4-(Chloromethylthio) benzyl alcohol (see Preparation 17) (5 mmol) in $CH_2Cl_2$ (2 ml) was added dropwise with stirring to a solution prepared from 5-chloropyrimidin-2-one hydrochloride (4 mmol) and triethylamine (8 mmol) in $CH_2Cl_2$ (20 ml). The resultant mixture was heated under reflux for 24 hours. The solvent was then distilled off, the residue triturated with water, dried ($MgSO_4$), triturated with ether and the residual material recrystallized from ethanol/Pet. ether. Yield 0.17 g (15%). $^1H$ NMR (DMSO-$d_6$, $\delta$) 4.50 ($CH_2O$), 5.22 ($CH_2S$), 7.22 (Ph), 8.03 or 8.50 (H-4, H-6, J3 Hz).

Pharmaceutical Composition Examples

Example A

Injection Solution

1. Active ingredient: 50 mg
2. Polysorbate 80:2.50 mg
3. Sodium chloride: 45 mg
4. Water for injection: to 5.0 ml The sterile active ingedient, precipitated as a very fine powder, is dispersed aseptically in an aqueous vehicle containing the wetting agent (Polysorbate 80) and sufficient sodium chloride to produce an approximately isotonic solution thus providing a suspension which may be used for deep intramuscular injection. Buffer salts may be incorporated (with a consequent reduction in the quantity of sodium chloride) to provide a suspension at the appropriate pH to ensure optimum stability of the compound before injection. The product may be presented as a dry filled vial of active ingredient together with a sterile ampoule of the remaining ingredients to permit extemporaneous preparation of the suspension immediately before injection.

EXAMPLE B

Injection Solution

1. Active ingredient: 100 mg
2. Aluminium monostearate: 5 mg
3. Fractionated coconut oil: to 1 ml Sterile active ingredient in the form of a very fine powder is dispersed aspectically in a sterile oily vehicle containing a suspending agent whose structure is built up during the heat sterilisation of the vehicle. Such a product may be presented as a pre-prepared suspension for intra-muscular injection. The dose administered may be adjusted by alteration of the dose volume. The product may be presented in multidose vials and sealed with oil resistant rubber plugs to permit withdrawal of the required dose volume.

We claim:

1. Compounds of the general formula:

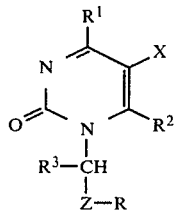

wherein

X represents a halogen atom or a trifluoromethyl group;

$R^1$ and $R^2$, independently represent a hydrogen atom or a $C_{1-6}$ alkyl group;

Z represents an oxygen atom or a sulfur atom or an oxide thereof or a group $>NR^4$ wherein $R^4$ is as defined for R hereinafter or represents the group $COR^5$ in which $R^5$ represents a hydrogen atom or a $C_{1-6}$ alkyl or a $C_{1-6}$ alkoxy group optionally substituted by one or more substituents selected from halogen atoms, hydroxyl, amino, oxo, or $C_{1-4}$ alkyl groups;

R represents a $C_{6-10}$ carbocyclic aromatic group which may carry one or more $C_{1-4}$ alkyl or phenyl groups said groups being optionally substituted by one or more substituents selected from halogen atoms, hydroxyl or $C_{1-6}$ alkoxy, amino or $C_{1-6}$ alkylamino, nitro, oxo, sulfonic acid and sulfonamido and thioether groups and oxides thereof;

$R^3$ represents a hydrogen atom or a $C_{1-6}$ alkyl, $C_{2-6}$ alkenyl, $C_{2-6}$ alkynyl, $C_{1-6}$ alkanoyl, $C_{2-6}$ alkenoyl, $C_{7-16}$ aralkyl or $C_{6-10}$ aryl group; and where acid or basic groups are present, the salts thereof.

2. Compounds as claimed in claim 1 wherein R represents a phenyl group optionally substituted by one or more substituents selected from halogen atoms, $C_{1-4}$ alkyl, $C_{1-4}$ haloalkyl, $C_{1-4}$ hydroxyalkyl, nitro and $C_{1-4}$ alkanyl groups.

3. Compounds as claimed in claim 2 wherein R represents a phenyl group optionally substituted by a fluorine, chlorine, methyl, methoxy, trifluoromethyl, hydroxymethyl, methoxycarbonyl, nitro and/or acetyl group.

4. Compounds as claimed in claim 1 which are
1-(4-chlorophenoxy)methyl-5-bromopyrimidin-2-one;
1-(3-tolylsulphenyl)methyl-5-chloropyrimidin-2-one;
1-(4-methoxyphenylsulphenyl)methyl-5-chloropyrimidin-2-one; or
1-(4-nitrophenylsulphenyl)methyl-5-chloropyrimidin-2-one.

5. A compound as claimed in claim 1 which is 1-(4-chlorophenoxy)methyl-5-iodopyrimidin-2-one.

6. Compounds as claimed in claim 1, wherein R represents optionally substituted phenyls or naphthyls.

7. Compounds as claimed in claim 2, wherein $R_1$, $R_2$, and $R_3$ each represent a hydrogen atom, Z represents an oxygen or sulphur atom and X represents a halogen atom.

8. Compounds as claimed in claim 3, wherein $R_1$, $R_2$, and $R_3$ each represent a hydrogen atom, Z represents an oxygen or sulphur atom and X represents a halogen atom.

* * * * *